(12) United States Patent
Liu

(10) Patent No.: US 9,204,800 B2
(45) Date of Patent: Dec. 8, 2015

(54) LOW COST HIGH EFFICIENCY SIGNAL INTERROGATION FOR MULTI-CHANNEL OPTICAL COHERENCE TOMOGRAPHY

(75) Inventor: Yu Liu, Irvine, CA (US)

(73) Assignee: ST. JUDE MEDICAL, INC., St. Paul, MN (US)

( * ) Notice: Subject to any disclaimer, the term of this patent is extended or adjusted under 35 U.S.C. 154(b) by 686 days.

(21) Appl. No.: 13/041,559

(22) Filed: Mar. 7, 2011

(65) Prior Publication Data

US 2012/0229812 A1 Sep. 13, 2012

(51) Int. Cl.
*G01B 9/02* (2006.01)
*A61B 5/00* (2006.01)

(52) U.S. Cl.
CPC .......... *A61B 5/0066* (2013.01); *G01B 9/02004* (2013.01); *G01B 9/0205* (2013.01); *G01B 9/02027* (2013.01); *G01B 9/02057* (2013.01); *G01B 9/02069* (2013.01); *G01B 9/02091* (2013.01); *G01B 2290/45* (2013.01)

(58) Field of Classification Search
USPC .......................... 356/477, 479; 702/155, 159
See application file for complete search history.

(56) References Cited

U.S. PATENT DOCUMENTS

| | | | |
|---|---|---|---|
| 6,775,007 B2 | 8/2004 | Izatt et al. | |
| 7,206,076 B2* | 4/2007 | Blalock | 356/503 |
| 7,391,520 B2 | 6/2008 | Zhou et al. | |
| 7,852,485 B2* | 12/2010 | Alphonse et al. | 356/479 |
| 8,182,142 B2* | 5/2012 | Abe et al. | 374/129 |
| 2006/0044566 A1 | 3/2006 | Li | |
| 2007/0127932 A1* | 6/2007 | Qi et al. | 398/188 |
| 2007/0278389 A1 | 12/2007 | Ajgaonkar et al. | |
| 2008/0175465 A1 | 7/2008 | Jiang et al. | |
| 2008/0234972 A1 | 9/2008 | Tsukada et al. | |
| 2009/0199646 A1 | 8/2009 | Sakamoto et al. | |
| 2009/0213387 A1 | 8/2009 | Nakabayashi et al. | |
| 2010/0041986 A1 | 2/2010 | Nguyen et al. | |
| 2012/0099112 A1* | 4/2012 | Alphonse et al. | 356/479 |
| 2012/0229812 A1 | 9/2012 | Liu | |
| 2013/0010302 A1* | 1/2013 | Sharma et al. | 356/479 |

FOREIGN PATENT DOCUMENTS

EP 1 744 119 A1 1/2007

OTHER PUBLICATIONS

Nakaji; "Optical Coherence Tomography with a multi-fiber array in sample arm"; Optical Fiber Technology; 2010; vol. 16; pp. 476-479.

* cited by examiner

*Primary Examiner* — Tarifur Chowdhury
*Assistant Examiner* — Jonathon Cook
(74) *Attorney, Agent, or Firm* — Mattingly & Malur, PC

(57) ABSTRACT

A signal interrogation system comprises an optical coupler to split input laser beam into a first laser beam as a power reference and a second laser beam, the optical coupler being coupled to a first path for the first laser beam and a second path for the second laser beam; an optical circulator disposed in the second path; a bi-directional optical switch disposed in the second path and having on one side a single channel end oriented toward the optical circulator and on another side multiple channel ends with multiple switchable channels; a plurality of optical fibers coupled to the multiple channel ends of the bi-directional optical switch; an interference optical signals path coupled to the optical circulator to receive the interference optical signals from the bi-directional switch; and a balanced photo detector to measure a power difference between the interference optical signals and the power reference.

20 Claims, 5 Drawing Sheets

LOW COST HIGH EFFICIENCY SIGNAL INTERROGATION FOR MULTI-CHANNEL OPTICAL COHERENCE TOMOGRAPHY

BACKGROUND OF THE INVENTION

The present invention relates generally to imaging and, more specifically, to a low cost high efficiency signal interrogation technique for multi-channel optical coherence tomography.

When lights reflected from samples interfere with a reference beam, the frequencies of the interfering signals reveal the depth where the light is reflected. This technique has been used in imaging, known as Optical Coherence Tomography (OCT). OCT is an optical signal acquisition and processing method allowing extremely high-quality, micrometer-resolution, three-dimensional images from within optical scattering media (e.g., biological tissue) to be obtained. In contrast to other optical methods, OCT, an interferometric technique typically employing near-infrared lights, is able to penetrate significantly deeper into the scattering medium, for example about three times deeper than confocal microscopy.

The first generation OCT is a time domain technique that uses a wideband light source and a time delay scanner. Only when the optical paths of the reflection lights and the reference beam are matched, they can interfere and be detected. The significant drawback of this technique is a low imaging speed, which is limited by the speed of the delay line scanner.

In order to improve the imaging speed, a second type of OCT called Spectral Domain OCT (SD-OCT) has been developed. Similar to the time domain OCT, this technique also uses a broadband light source. Instead of the time delay scanner, a transmission grating and a CCD array are used to interrogate the interfering signals. Since the speed for CCD array scanning can be very high, this technique can be used for very high speed 3D imaging. The disadvantages, however, are the heightened costs, the limited imaging depth and resolution.

Fourier domain OCT (FD-OCT) that uses wavelength-swept fiber laser sources is the third type of OCT. The coherence length resulting from the narrow instantaneous laser linewidth enables imaging up to 4 mm depth in tissue. The wavelength sweeping rate has reached 100 kHz, which is fast enough for 3D imaging in many applications. Of the three typical OCT techniques described above, FD-OCT that uses wavelength-swept light sources is the most suitable for commercial purposes in biomedical imaging; this technique is cost effective, and has a faster imaging rate as well as improved resolution and sensitivity.

When a wavelength-swept light source and a fiber probe are used in OCT imaging, a 1D depth image, or A-scan, is obtained when the laser source makes a complete scan. When the fiber probe is scanned across an object, a series of A-scans produce a 2D cross-section image, or B-scan. When a series of 2D section imaging are accumulated, a 3D image is obtained.

For some applications, however, the process of scanning may be inconvenient or not economical, such as in catheter imaging. Probe arrays could be used instead of scanning to form a multi-channel OCT. The prototyped 5-channel OCT has been developed by Thorlabs, using an optical switch, with five photo detectors and fiber circulators, to measure five channel signals, respectively, as shown in FIG. 1. For a 16-channel OCT, the cost for the signal interrogation would be over $30,000 at the time of drafting this patent application. Such a high cost renders it unsuitable for commercial purposes. Apart from the high cost, the cross-talking, and the bulk size, the most critical drawback is that this interrogation technique is not suitable for a balanced detection to remove the strong low frequency signal background, which seriously reduces the measurement sensitivity.

Multi-channel OCT can be used to measure multiple distances that could be used to investigate in real time strain, force, temperature, and the like. When a force is applied to a spring or an elastic material, three channels OCT can monitor in real time three distances that could be used to measure the force directions and its amplitude. If the distance changes as a result of a thermal expansion material, one channel OCT could be used to measure temperature in real time.

BRIEF SUMMARY OF THE INVENTION

In various applications such as OCT (Optical Coherence Tomography) imaging for imaging biological tissue or the like, it is desirable to provide balanced detection in the signal interrogation process, preferably at high efficiency and low cost.

In accordance with an aspect of the present invention, a signal interrogation system comprises an optical coupler to split input laser beam into a first laser beam as a power reference and a second laser beam, the optical coupler being coupled to a first path for the first laser beam and a second path for the second laser beam; an optical circulator disposed in the second path; a bi-directional optical switch having on one side a single channel end and on another side multiple channel ends with multiple switchable channels, the bi-directional optical switch being disposed in the second path, with the single channel end oriented toward the optical circulator; a plurality of optical fibers coupled to the multiple channel ends of the bi-directional optical switch, wherein the bi-directional optical switch switches the second laser beam among the plurality of optical fibers coupled to the multiple switchable channels, the plurality of optical fibers directing the second laser beam to a target and receiving interference optical signals based on reflection/scattering lights of the second laser beam from the target; an interference optical signals path coupled to the optical circulator to receive the interference optical signals from the bi-directional switch; and a balanced photo detector to measure a power difference between the interference optical signals and the power reference.

In some embodiments, the system further comprises an optical imaging device coupled to the plurality of optical fibers to deliver the laser beam from the optical fibers to illuminate the target, to generate reflection at a fiber end face of a fiber probe of the optical imaging device, to receive reflection/scattering lights from the target, and to direct the interference optical signals resulting from interfering between the reflection at the fiber end face and the reflection/scattering at the target to the plurality of optical fibers. The fiber probe of the optical imaging device is configured to deliver the second laser beam to illuminate the target through fiber GRIN lenses, the fiber GRIN lenses receiving reflection/scattering lights from the target to interfere with reference lights reflected at the fiber end face. The interference optical signals are generated from the target reflection/scattering lights and the reference lights.

In specific embodiments, the system further comprises a variable optical attenuator disposed in the first path between the optical coupler and the photo detector. The variable optical attenuator is controlled to match power of the first laser beam and the interference optical signals directed to the photo detector. The photo detector is tunable to adjust a gain, or the photo detector has a fixed gain. The optical coupler is configured to split the input laser beam into about 1% power for the first laser beam and about 99% power for the second laser beam; and the bi-directional optical switch has 16 switchable channels.

In accordance with another aspect of the invention, a signal interrogation system comprises a bi-directional optical switch having on one side a single channel end and on another side multiple channel ends with multiple switchable channels, the bi-directional optical switch being disposed in a path of a laser beam, with the single channel end oriented to receive the laser beam, the multiple channel ends directing the laser beam to illuminate an imaging target and generate reflection/scattering lights from the imaging target and to generate reflection lights from a reference surface, so as to produce interference optical signals resulting from the reflection lights at the reference surface and the reflection/scattering lights at the imaging target; a mechanism coupled to the single channel end of the bi-directional optical switch to receive the interference optical signals and to reduce background of laser source intensity profiles from the interference optical signals; and a photo detector to measure the interference optical signals from the mechanism.

In some embodiments, the system further comprises means coupled to the multiple channel ends of the bi-directional optical switch, for delivering the laser beam to illuminate the imaging target and generate the reflections/scattering lights from the imaging target and the reference surface, and directing the interference optical signals to the multiple channel ends of the bi-directional optical switch. The mechanism comprises an optical coupler disposed in the path of the laser beam upstream of the bi-directional optical switch to split a portion of the laser beam and direct the portion of the laser beam as a power reference toward the photo detector; and means for matching power between the power reference and the interference optical signals directed to the photo detector. The mechanism comprises an electronic high-pass filter configured to reduce the background of laser source intensity profiles from the interference optical signals. The bi-directional optical switch has at least 16 switchable channels.

In accordance with another aspect of this invention, a signal interrogation system comprises a bi-directional optical switch having on one side a single channel end and on another side multiple channel ends with multiple switchable channels, the bi-directional optical switch being disposed in a path of a laser beam, with the single channel end oriented to receive the laser beam; a plurality of optical fibers coupled to the multiple channel ends of the bi-directional optical switch, wherein the bi-directional optical switch switches the laser beam among the plurality of optical fibers coupled to the multiple switchable channels, the plurality of optical fibers directing the laser beam to illuminate a target and receiving reflection/scattering lights from the target and receiving reflection lights from a reference surface, so as to produce interference optical signals between the reflection/scattering lights from the target and the reflection lights from the reference surface; a mechanism to reduce background of laser source intensity profiles from the interference optical signals; means for directing the interference optical signals from the single channel end of the bi-directional switch to the mechanism; and a photo detector disposed downstream of the mechanism to receive the interference optical signals.

In some embodiments, the system further comprises means for delivering the laser beam from the optical fibers to illuminate the target to generate the reflection/scattering lights from the target and to the reference surface to generate the reflection lights from the reference surface, and directing the interference optical signals to the plurality of optical fibers.

These and other features and advantages of the present invention will become apparent to those of ordinary skill in the art in view of the following detailed description of the specific embodiments.

BRIEF DESCRIPTION OF THE DRAWINGS

FIG. 3($b$) schematically illustrates a fiber probe with a cleaved bare fiber; and FIG. 3($c$) schematically illustrates a fiber probe with a fiber GRIN lens that is used to form a fiber probe array for imaging.

FIG. 6($b$) is a plot of the signals of three channels OCT showing three distances between GRIN lenses and reflection surfaces.

DETAILED DESCRIPTION OF THE INVENTION

Figure 1:
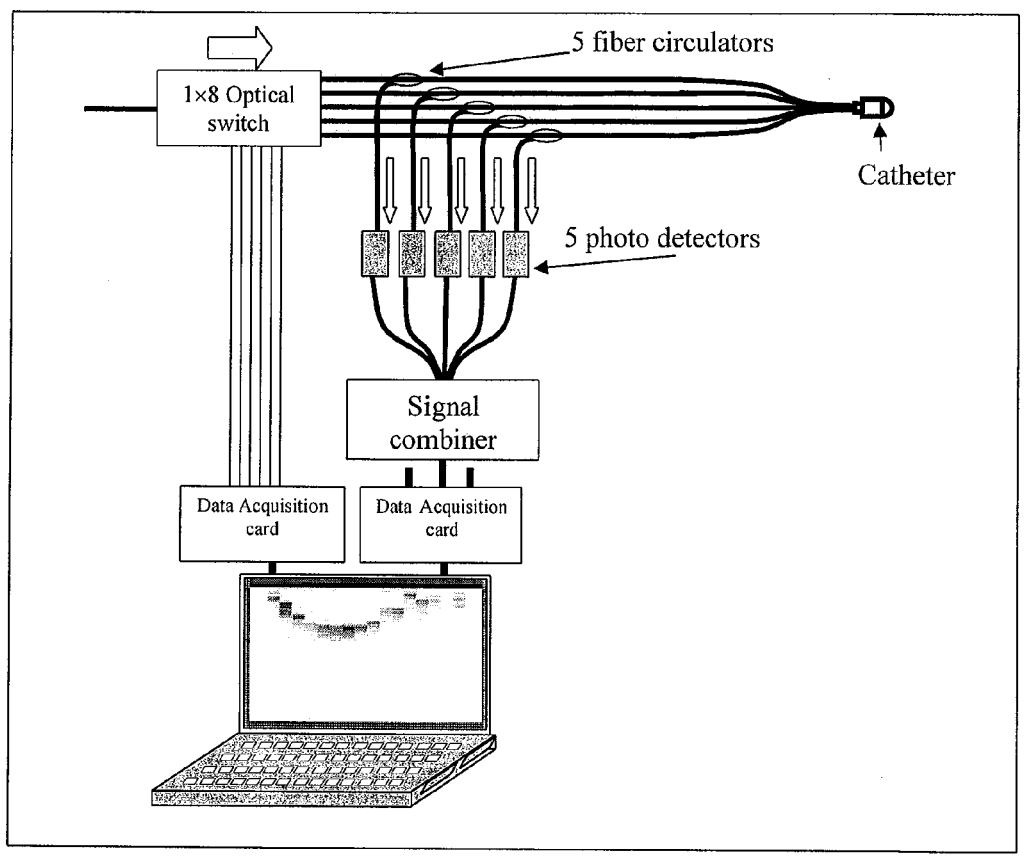
FIG. 1 is a schematic diagram illustrating a 5-channel OCT signal interrogation system having five detectors, five fiber circulators, an optical switch, and a signal combiner.

In the following detailed description of the invention, reference is made to the accompanying drawings which form a part of the disclosure, and in which are shown by way of illustration, and not of limitation, exemplary embodiments by which the invention may be practiced. In the drawings, like numerals describe substantially similar components throughout the several views. Further, it should be noted that while the detailed description provides various exemplary embodiments, as described below and as illustrated in the drawings, the present invention is not limited to the embodiments described and illustrated herein, but can extend to other embodiments, as would be known or as would become known to those skilled in the art. Reference in the specification to "one embodiment," "this embodiment," or "these embodiments" means that a particular feature, structure, or characteristic described in connection with the embodiment is included in at least one embodiment of the invention, and the appearances of these phrases in various places in the specification are not necessarily all referring to the same embodiment. Additionally, in the following detailed description, numerous specific details are set forth in order to provide a thorough understanding of the present invention. However, it will be apparent to one of ordinary skill in the art that these specific details may not all be needed to practice the present invention. In other circumstances, well-known structures, materials, circuits, processes and interfaces have not been described in detail, and/or may be illustrated in block diagram form, so as to not unnecessarily obscure the present invention.

In the following description, relative orientation and placement terminology, such as the terms horizontal, vertical, left, right, top and bottom, is used. It will be appreciated that these terms refer to relative directions and placement in a two dimensional layout with respect to a given orientation of the layout. For a different orientation of the layout, different relative orientation and placement terms may be used to describe the same objects or operations.

Exemplary embodiments of the invention, as will be described in greater detail below, provide apparatuses and methods for low cost high efficiency signal interrogation technique for multi-channel optical coherence tomography.

Figure 2:
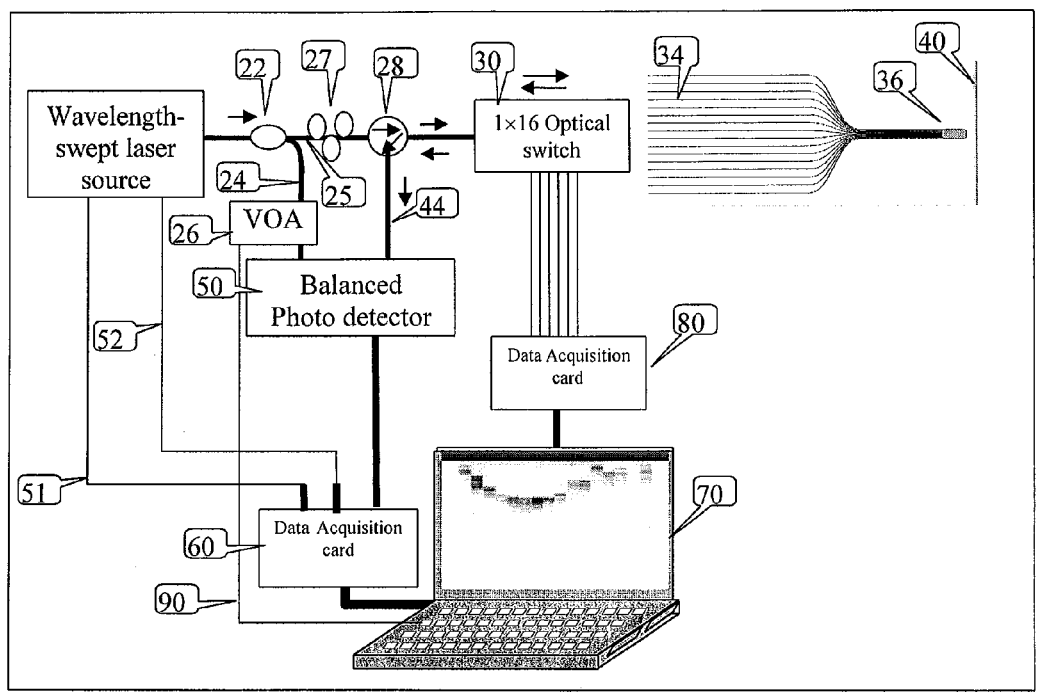
FIG. 2 is a schematic diagram illustrating a signal interrogation system for multi-channel OCT using only one photo detector and one fiber circulator according to an embodiment of the present invention.

FIG. 2 is a schematic diagram illustrating a signal interrogation system for multi-channel OCT using only one photo detector and one fiber circulator according to an embodiment of the present invention. Such a configuration provides multi-channel OCT that is cost-effective and efficient for commercial purposes. In this interrogation process, the optical switch is only required to act as a bidirectional device. An added benefit is that the cost of a bidirectional optical switch can be even lower than that of a single directional optical switch. For 5 and 16 channels, the costs for the signal interrogation are about 20% and 6% of the costs for the current design as shown in FIG. 1. These costs are estimated at the time of drafting this patent application.

As seen in FIG. 2, the signal interrogation system includes a 1/99 optical coupler 22, which splits the incident laser beam from a wavelength-swept laser source into two beams propagating along two paths. The first beam (path 24) with ~1% incident laser power passes a variable optical attenuator (VOA) 26 as a power reference, while the second beam (path 25) with ~99% incident laser power couples to the optical circulator port-1 and emits at port-2 of the optical circulator 28. A polarization controller 27 may be provided upstream of the optical circulator 28 to align the input laser polarization to the circulator 28. The emitting lights from the optical circulator port-2 connects to a 1×16 optical switch 30. The 1×16 optical switch 30 has on one side one single channel end (e.g., for single input) and on the opposite side multiple channel ends with multiple (16) switchable channels (e.g., for multiple outputs). Other examples of multiple switchable channel optical switches usually include 1×2, 1×4, 1×8, 1×2$^N$ (N=1, 2, 3, . . . ). It is a two-way switch that, in one direction, switches the incident lights among 16 channels of optical fibers 34 leading to a fiber array (part of an imaging device 36 such as a catheter), which directs the incident lights to illuminate the target 40. The reflection or scattering lights from the target 40 will couple back to the same fiber and interfere with the lights reflected at the fiber end face (see 100 in FIG. 3). The interference optical signals propagate back via the channels 34 and the 1×16 optical switch 30 in the opposite direction to port-2 of the optical circulator 28. The optical circulator 28 directs the interference optical signals from port-2 to port-3 (path 44) as target interfered optical signals. The power reference path 24 and the target interfered optical signals path 44 both lead to a balanced photo detector 50. A balanced photo detector 50 is a detector that is configured to measure the power difference between two inputs. The output of the balanced photo detector 50 is directed to a data acquisition card 60 (e.g., ATS460) for analog digital convert (ADC) or data acquisition and processing such as Fast Fourier Transform (FFT) by a computer 70. Meanwhile, the laser source sends a trigger signal via a trigger signal line 51 to trigger the data acquisition card 60 to start capturing data, and sends an MZI clocking signal via a clocking signal line 52 to re-clock the measured interference signal from equidistant time spacing into equidistant frequency spacing. The computer 70 employs another data acquisition card 80 (e.g., NI PC6731) to control the 1×16 optical switch 30. The computer 70 is further coupled to the variable optical attenuator 26 via a control line 90. The computer 70 can also display the imaging. Note that if the data acquisition card 60 has enough digital line outputs to control the 1×16 optical switch, the second data acquisition card 80 is not required.

FIG. 3(a) is a photograph of ablation catheters employed with a 16 fibers array for OCT imaging; FIG. 3(b) schematically illustrates a fiber probe with a cleaved bare fiber; and FIG. 3(c) schematically illustrates a fiber probe with a fiber GRIN lens. The fiber probes are used to form a fiber probe array for imaging (imaging device 36). The emitting lights from the fiber array (imaging device 36) illuminate the target 40 and the reflection/scattering lights from the target 40 re-couple back to the fiber array (imaging device 36). The reflection lights include object reflection/scattering from the target 40 and reflection from the fiber end face 100 of the imaging device 36 which serves as reference lights for the target reflection. The reference lights interfere with the target reflection/scattering lights and produce interference signals for imaging the target 40.

In FIG. 2, the variable optical attenuator 26 in the path 24 is controlled by the computer 70 via the control line 90 to perform several functions. It matches the power in the path 24 with the power of the interference signals in the path 44. The computer-controlled variable optical attenuator 26 and balanced photo detector 50 can be used to automatically remove the strong background of low frequency laser power profiles from the interference signals to increase the measurement sensitivity.

The photo detector 50 takes in the power reference from the path 24 and the interference optical signals from the path 44. It converts optical signals into analog electronic signals that represent the interference generated by lights reflected from the target 40 and corresponding fiber end face. For example, if the target 40 is a tissue, the frequency of the interference signal indicates the depth where the light reflection or scattering occurs. A fast data acquisition card can be employed to convert the analog signal into a digital signal. A Fast Fourier Transform (FFT) can be used to determine the frequency to reveal the reflection/scattering depth for imaging. It is worth to note that the converted digital data stream could be in equidistant time spacing, which is required for re-clocking into an equidistant frequency spacing.

Figure 4:
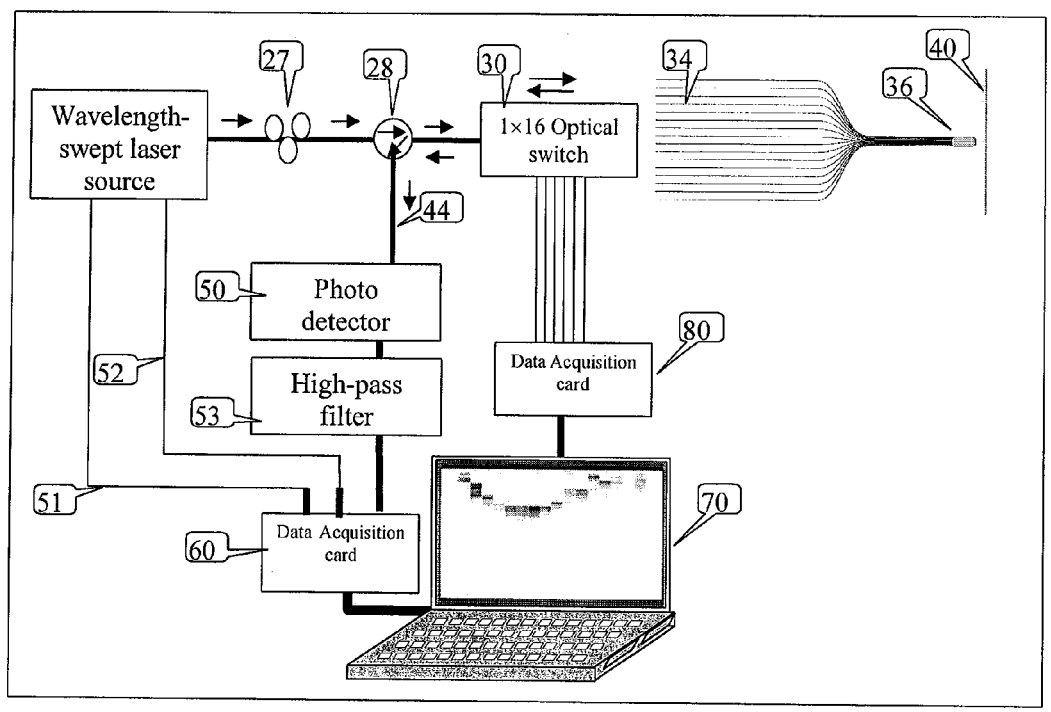
FIG. 4 is a schematic diagram illustrating a signal interrogation system in which a high-pass filter is used to filter signals upstream of the photo detector according to another embodiment of the invention.

FIG. 4 is a schematic diagram illustrating a signal interrogation system in which a high-pass filter is used to filter signals upstream of the photo detector according to another embodiment of the invention. This embodiment involves another investigation approach that eliminates the 1/99 coupler 22, VOA 26, and power reference 24 that are present in the embodiment of FIG. 2. In this investigation technique, only one interference optical signal connects to one input of the balanced photo detector, and the detected electronic signal will have a strong background of laser source intensity profiles, which would degrade the measurement sensitivity. An electronic high-pass filter 53 is used to filter this background to improve the measurement sensitivity. Since there is not balanced detection in this investigation technique, a single input regular photo detector 50' can be used to measure the interference optical signals.

Figure 5:
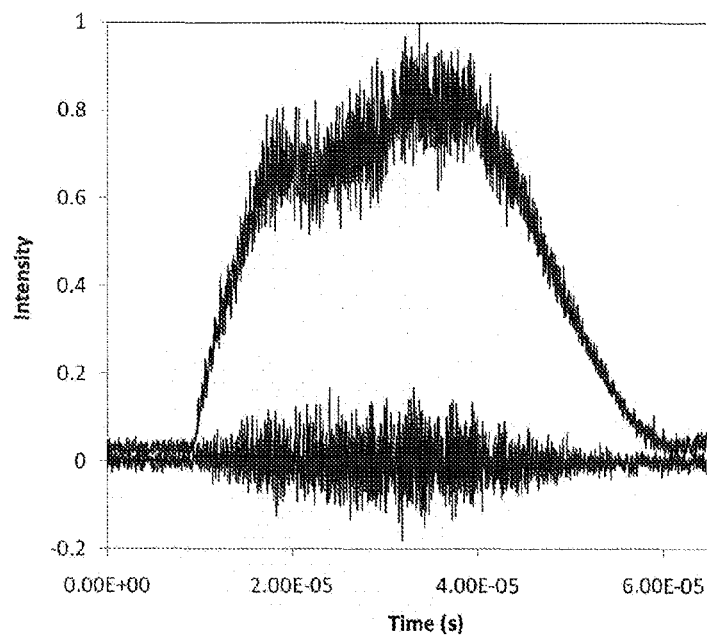
FIG. 5 shows an intensity plot of two typical interference signals that were measured without balanced detection to illustrate the function of a high-pass filter for filtering the background laser source intensity profiles.

FIG. 5 shows an intensity plot of two typical interference signals that were measured without balanced detection to illustrate the function of a high-pass filter for filtering the background laser source intensity profiles. The upper curve is measured without a high-pass filter while the lower curve is measured with a high pass filter. The high-pass filter removes the strong background of the laser source profile.

Significantly, the present signal interrogation method provides a balanced detection that removes strong signal backgrounds, where a 1/99 coupler 22 is used to provide a power reference. This measurement technique is referred to as a reference power matched balanced detection, where a variable optical attenuator 26 may be involved to match the power.

Figure 3:
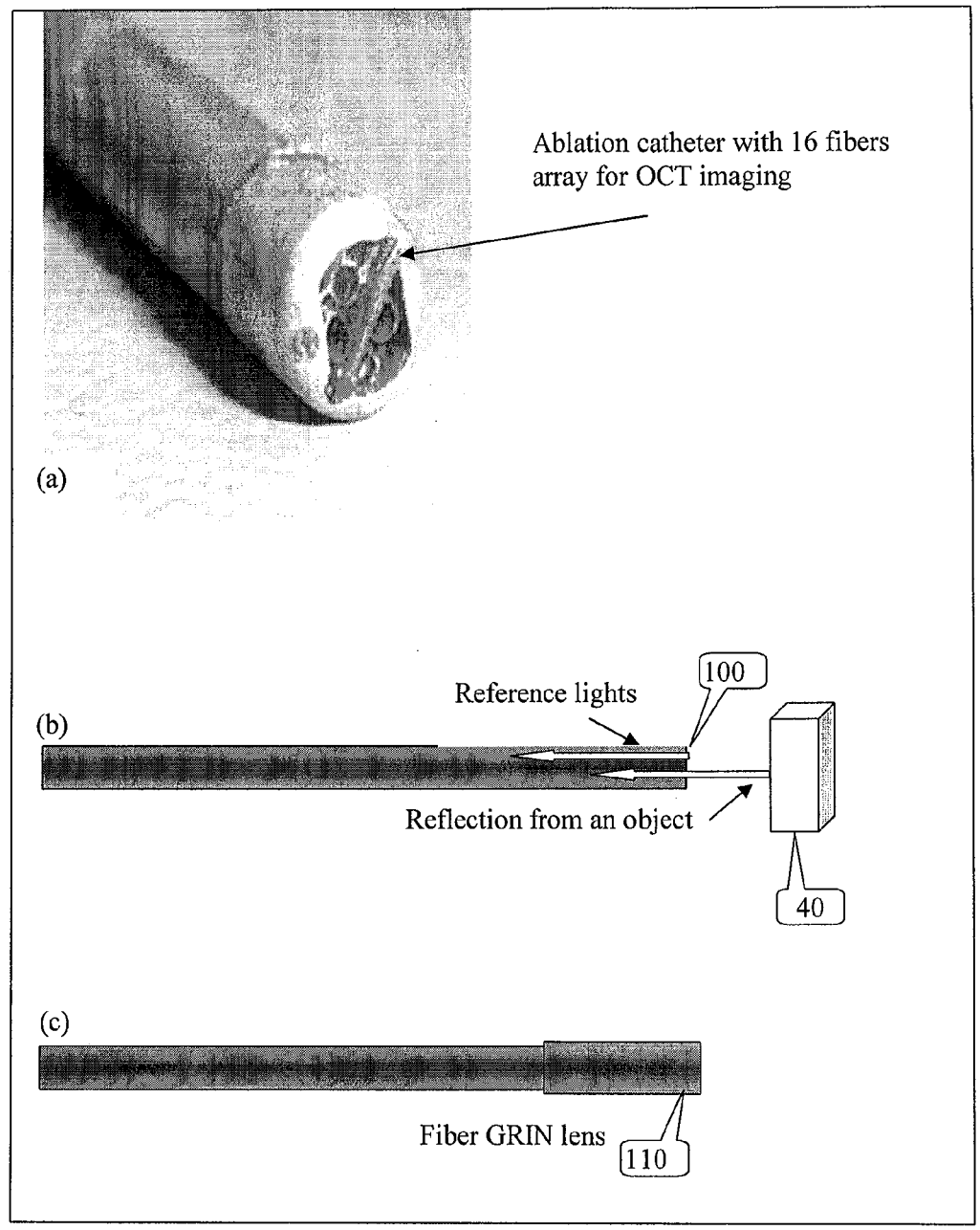
FIG. 3($a$) is a photograph of ablation catheters employed with a 16 fibers array for OCT imaging.

In addition, the system employs a fiber array (16 channels 34 in FIG. 2) in conjunction with a single bi-directional optical switch (1×16 optical switch 30 in FIG. 2) to simulate the scanning to achieve 2D/3D imaging, so that no optical scanning is required. This is advantageous when optical scanning is very difficult or not economical. As discussed above, the reflection from the fiber end face 100 of the imaging device 36 can be used as a reference for the target reflection/scattering signals reflected from the target 40, as shown in FIG. 3. The fiber tip of the imaging device 36 may be configured to be angle cleaved or coated to a desired reflectance (i.e., ~1% in air). In order to collimate the exit beam, a gradient-index (GRIN) fiber lens 110 can be spliced onto the fiber probe.

Furthermore, the use of a single bi-directional 1×16 optical switch 30 enables the use of a single interference signals path 44 to be used to direct the interference optical signals from the optical circulator 28 to a single photo detector 50. This eliminates the cost of additional photo detectors, fiber circulators, and signal combiner, and allows the system to be made economically and compactly.

Figure 6:
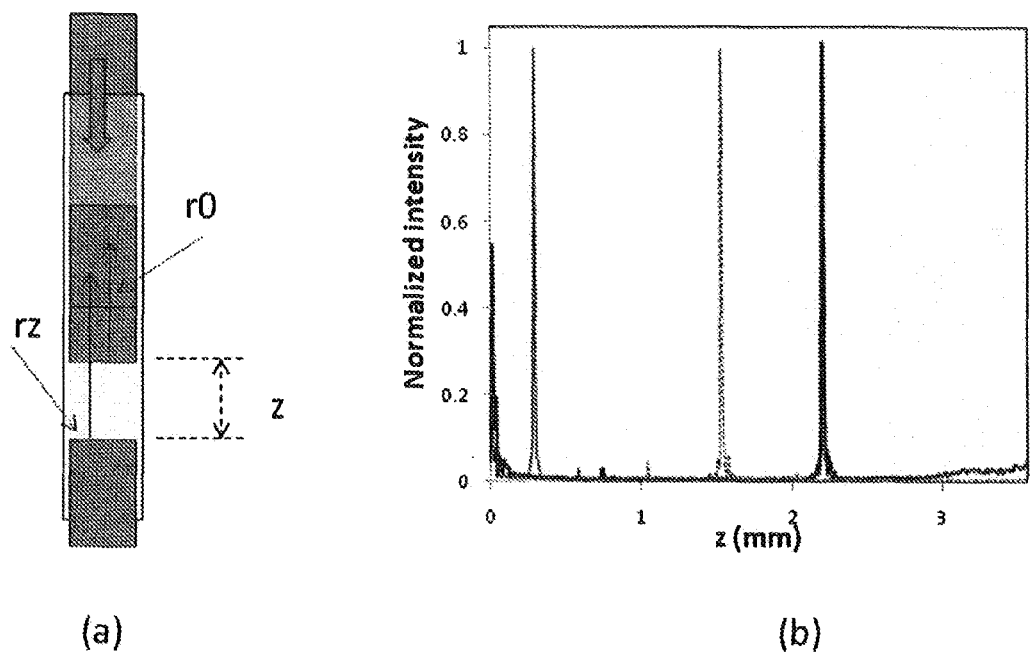
FIG. 6($a$) is a schematic diagram illustrating one channel OCT for distance measurement that could be used to measure force or temperature.

For distance measurement, the interferometer is shown in FIG. 4, the intensity of the interfering signal for one channel is given as $$I = \left| r_0 + r_z e^{j\frac{\pi \cdot 4z}{\lambda_0 + \Delta\lambda \sin(2\pi f_{sweep} t)}} \right|^2, \quad (1)$$

where $r_0$ is the amplitude reflectance at the fiber end face and $r_z$ is the amplitude reflectance at z depth of a target imaging object or the gap between fiber and reflection surface as shown in FIG. 6. FIG. 6(*a*) is a schematic diagram illustrating one channel OCT for distance measurement that could be used to measure force or temperature. FIG. 6(*b*) is a plot of the signals of three channels OCT showing three distances between GRIN lenses and reflection surfaces. $\lambda_0$ is the central wavelength and $\Delta\lambda$ is the wavelength sweeping range. $f_{sweep}$ is the wavelength sweeping rate and $\Delta\lambda_{fwhm}$ is the laser instantaneous linewidth. For simplicity, a top-hat spectral profile $$f(\delta\lambda) = \begin{cases} 1 & |\delta\lambda| \leq \Delta\lambda_{fwhm}/2 \\ 0 & |\delta\lambda| > \Delta\lambda_{fwhm}/2 \end{cases}$$

is used. Eq. (1) can be simplified to Eq. (2), and the interfering signal is expressed as $$I \sim 2r_o r_z \cos\left[\frac{4\pi \cdot z}{\lambda_0 + \Delta\lambda \sin(2\pi f_{sweep} t)}\right], \quad (2)$$

where the DC components $r_0^2 + r_z^2$ are ignored.

When a Fast Fourier Transform (FFT) is applied to Eq. (2), the Fourier frequency F is directly proportional to the depth z. Note that a re-clocking operation to achieve an equidistant spacing in frequency is required for the data stream when it is captured in equidistant time spacing.

$$z = \frac{\lambda_0^2}{2\Delta\lambda} \cdot \frac{F}{f_{sweep}}, \quad (3)$$

When the spatial displacements result from the applied force and the applied force is directly proportional to the displacements in a linear system, the displacements can be expressed as $$\begin{bmatrix} \Delta x_1 \\ \Delta x_2 \\ \Delta x_3 \end{bmatrix} = \begin{bmatrix} A_{1x} & A_{1y} & A_{1z} \\ A_{3x} & A_{2y} & A_{2z} \\ A_{3x} & A_{3y} & A_{3z} \end{bmatrix} \begin{bmatrix} F_x \\ F_y \\ F_z \end{bmatrix} \quad (4)$$

where $\lambda_{ij}$, i=1, 2, 3, j=x, y, z are the nine coefficients related to the mechanical structures and material strengths that can be determined by experiments. $\lambda x_i$, i=1, 2, 3 indicate the three displacements that can be calculated by Eq. (3). Rearranging Eq. (4), the three force components are obtained as $$\begin{bmatrix} F_x \\ F_y \\ F_z \end{bmatrix} = M^{-1} \begin{bmatrix} \Delta x_1 \\ \Delta x_2 \\ \Delta x_3 \end{bmatrix}, \quad (5)$$

where $$M = \begin{bmatrix} A_{1x} & A_{1y} & A_{1z} \\ A_{2x} & A_{2y} & A_{2z} \\ A_{3x} & A_{3y} & A_{3z} \end{bmatrix}. \quad (6)$$

The force value and the direction angles are obtained as $$\begin{cases} F = \sqrt{F_x^2 + F_y^2 + F_z^2} \\ \alpha = \cos^{-1}(F_x/F) \\ \beta = \cos^{-1}(F_y/F) \end{cases} \quad (7)$$

where $F_x$, $F_y$, and $F_z$ are the three components of the force. F, $\alpha$ and $\beta$ are the value and the direction angles of the force, respectively. When a computer controlled optical switch makes a scan from channel 1 to 3 to acquire displacements, the value and direction angles of the applied force can be real-time measured.

Three fibers are needed to measure three components of force. The direction and amplitude of the force can be calculated from the three components. Note that a calibration is required for the calculation of the value of the force and its direction.

When the displacement results from temperature, one channel OCT can be used to measure the temperature $$\text{Temperature} = k_t \cdot \frac{\lambda_0^2}{2\Delta\lambda} \cdot \frac{F}{f_{sweep}}, \quad (8)$$

where $k_t$ is the linear thermal/temperature expansion coefficient of the material that is used to convert temperature changes into spatial displacement which is captured by the optical fiber associated with the channel for measuring the temperature. For good sensitivity, a sufficiently large thermal/temperature expansion coefficient material is usually used to design a certain structure to achieve a length or spatial displacement due to thermal expansion/contraction. For example, a 100-m long glass fiber that has a thermal expansion coefficient of $0.5 \times 10^{-6}$ will expand by 50 µm when the temperature increases by 1 degree. Note that the refractive index of the fiber changes as well and the total optical length increases by about 750 µm. As such, the temperature change can be determined by measuring the change in this optical length of the fiber.

The multi-channel OCT can be used to measure in real time multiple displacements for sensing, such as force, temperature, and the like, where corresponding couplers are used to convert the force, temperature, and the like into spatial displacements. When a plate is moving or rotating, one-channel or multi-channel OCT can be used to monitor in real time the gap between the plate surface and the fiber to determine the range of the wave up and down. For 16-channel OCT, 4 channels could be assigned to sensing force and temperature, and the remaining 12 channels could be used for imaging.

In the description, numerous details are set forth for purposes of explanation in order to provide a thorough understanding of the present invention. However, it will be apparent to one skilled in the art that not all of these specific details are required in order to practice the present invention. Additionally, while specific embodiments have been illustrated and described in this specification, those of ordinary skill in the art appreciate that any arrangement that is calculated to achieve the same purpose may be substituted for the specific embodiments disclosed. This disclosure is intended to cover any and all adaptations or variations of the present invention, and it is to be understood that the terms used in the following claims should not be construed to limit the invention to the specific embodiments disclosed in the specification. Rather, the scope of the invention is to be determined entirely by the following claims, which are to be construed in accordance with the established doctrines of claim interpretation, along with the full range of equivalents to which such claims are entitled.

What is claimed is:

1. A signal interrogation system comprising:
    an optical coupler to split input laser beam into a first laser beam as a power reference and a second laser beam, the optical coupler being coupled to a first path for the first laser beam and a second path for the second laser beam;
    an optical circulator disposed in the second path;
    a bi-directional optical switch having on one side a single channel end and on another side multiple channel ends with multiple switchable channels, the bi-directional optical switch being disposed in the second path, with the single channel end oriented toward the optical circulator;
    a plurality of optical fibers coupled to the multiple channel ends of the bi-directional optical switch, wherein the bi-directional optical switch switches the second laser beam among the plurality of optical fibers coupled to the multiple switchable channels, the plurality of optical fibers directing the second laser beam to a target and receiving interference optical signals based on reflection/scattering lights of the second laser beam from the target, the interference optical signals for a given optical fiber of the plurality of optical fibers being produced by coupling back the reflection/scattering lights of the second laser beam from the target to the given optical fiber and interfering with lights reflected at a reference surface for the given optical fiber from the second laser beam;
    an interference optical signals path coupled to the optical circulator to receive the interference optical signals from the bi-directional optical switch;
    a balanced photo detector to measure a power difference between the interference optical signals and the power reference;
    a variable optical attenuator disposed in the first path between the optical coupler and the photo detector; and
    a computer coupled to the balanced photo detector to receive the measured power difference, and to the variable optical attenuator to control the variable optical attenuator to match power of the first laser beam as the power reference and the interference optical signals directed to the photo detector based on the measured power difference.

2. The signal interrogation system of claim 1, further comprising:
    an optical imaging device coupled to the plurality of optical fibers to deliver the laser beam from the optical fibers to illuminate the target, to generate reflection at a fiber end face of a fiber probe of the optical imaging device as the reference surface for the optical fibers, to receive reflection/scattering lights from the target, and to direct the interference optical signals resulting from interfering between the reflection at the fiber end face and the reflection/scattering at the target to the plurality of optical fibers.

3. The signal interrogation system of claim 2,
    wherein the fiber probe of the optical imaging device is configured to deliver the second laser beam to illuminate the target through fiber GRIN lenses, the fiber GRIN lenses receiving reflection/scattering lights from the target to interfere with reference lights reflected at the fiber end face;
    wherein the interference optical signals are generated from the target reflection/scattering lights and the reference lights.

4. The signal interrogation system of claim 1, further comprising:
    a control line coupled to the variable optical attenuator and the computer.

5. The signal interrogation system of claim 1,
    wherein the computer controls the variable optical attenuator and the balanced photo detector to automatically remove background of low frequency laser power profiles from the interference optical signals to increase measurement sensitivity.

6. The signal interrogation system of claim 1,
    wherein the photo detector is tunable to adjust a gain.

7. The signal interrogation system of claim 1,
    wherein the photo detector has a fixed gain.

8. The signal interrogation system of claim 1,
    wherein the optical coupler is configured to split the input laser beam into about 1% power for the first laser beam and about 99% power for the second laser beam; and
    wherein the bi-directional optical switch has 16 switchable channels.

9. The signal interrogation system of claim 1, further comprising:
    a data acquisition unit to receive data including the measured power difference from the balanced photo detector for analog to digital conversion or data acquisition and processing by the computer.

10. The signal interrogation system of claim 9, further comprising:
a laser source to deliver the input laser beam, to send a trigger signal to trigger the data acquisition unit to start capturing data, and to send an MZI clocking signal to the data acquisition unit to re-clock the interference optical signals from equidistant time spacing into equidistant frequency spacing.

11. A signal interrogation method comprising:
splitting, using an optical coupler, an input laser beam into a first laser beam as a power reference and a second laser beam, the optical coupler being coupled to a first path for the first laser beam and a second path for the second laser beam;
providing an optical circulator in the second path;
providing in the second path a bi-directional optical switch having on one side a single channel end and on another side multiple channel ends with multiple switchable channels, with the single channel end oriented toward the optical circulator;
coupling a plurality of optical fibers to the multiple channel ends of the bi-directional optical switch, the bi-directional optical switch switching the second laser beam among the plurality of optical fibers coupled to the multiple switchable channels, the plurality of optical fibers directing the second laser beam to a target and receiving interference optical signals based on reflection/scattering lights of the second laser beam from the target, the interference optical signals for a given optical fiber of the plurality of optical fibers being produced by coupling back the reflection/scattering lights of the second laser beam from the target to the given optical fiber and interfering with lights reflected at a reference surface for the given optical fiber from the second laser beam;
coupling an interference optical signals path to the optical circulator to receive the interference optical signals from the bi-directional optical switch;
measuring, using a balanced photo detector, a power difference between the interference optical signals and the power reference;
providing a variable optical attenuator in the first path between the optical coupler and the photo detector; and
coupling a computer to the balanced photo detector to receive the measured power difference, and to the variable optical attenuator to control the variable optical attenuator to match power of the first laser beam as the power reference and the interference optical signals directed to the photo detector based on the measured power difference.

12. The signal interrogation method of claim 11, further comprising:
coupling an optical imaging device to the plurality of optical fibers to deliver the laser beam from the optical fibers to illuminate the target, to generate reflection at a fiber end face of a fiber probe of the optical imaging device as the reference surface for the optical fibers, to receive reflection/scattering lights from the target, and to direct the interference optical signals resulting from interfering between the reflection at the fiber end face and the reflection/scattering at the target to the plurality of optical fibers.

13. The signal interrogation method of claim 12, further comprising:
delivering, using the fiber probe of the optical imaging device, the second laser beam to illuminate the target through fiber GRIN lenses, the fiber GRIN lenses receiving reflection/scattering lights from the target to interfere with reference lights reflected at the fiber end face;
wherein the interference optical signals are generated from the target reflection/scattering lights and the reference lights.

14. The signal interrogation method of claim 11, further comprising:
coupling a control line to the variable optical attenuator and the computer.

15. The signal interrogation method of claim 11, further comprising:
controlling the variable optical attenuator and the balanced photo detector to automatically remove background of low frequency laser power profiles from the interference optical signals to increase measurement sensitivity.

16. The signal interrogation method of claim 11, wherein the photo detector is tunable to adjust a gain.

17. The signal interrogation method of claim 11, wherein the photo detector has a fixed gain.

18. The signal interrogation method of claim 11, further comprising:
splitting, by the optical coupler, the input laser beam into about 1% power for the first laser beam and about 99% power for the second laser beam.

19. The signal interrogation method of claim 11, further comprising:
providing a data acquisition unit to receive data including the measured power difference from the balanced photo detector for analog to digital conversion or data acquisition and processing by the computer.

20. The signal interrogation method of claim 19, further comprising:
providing a laser source to deliver the input laser beam, to send a trigger signal to trigger the data acquisition unit to start capturing data, and to send an MZI clocking signal to the data acquisition card to re-clock the interference optical signals from equidistant time spacing into equidistant frequency spacing.

* * * * *